United States Patent [19]

Eldrige, Jr. et al.

[11] Patent Number: 5,036,866

[45] Date of Patent: * Aug. 6, 1991

[54] SURGICAL INSTRUMENT RETAINER

[75] Inventors: John D. Eldrige, Jr.; Mary A. Morgan, both of Newport Beach, Calif.

[73] Assignee: Devon Industries, Inc., Chatsworth, Calif.

[*] Notice: The portion of the term of this patent subsequent to Jul. 31, 2007 has been disclaimed.

[21] Appl. No.: 474,477

[22] Filed: Feb. 2, 1990

Related U.S. Application Data

[63] Continuation of Ser. No. 166,480, Mar. 9, 1988, Pat. No. 4,944,311.

[51] Int. Cl.⁵ .................... A61B 19/00; A61B 19/08
[52] U.S. Cl. ..................................... 128/849; 128/852
[58] Field of Search ........................... 128/849–856; 383/12, 13, 26, 51, 67; 206/570, 363, 370, 373, 438, 478, 483, 806, 818; 335/303; 428/129

[56] References Cited

U.S. PATENT DOCUMENTS

| | | | |
|---|---|---|---|
| 3,201,028 | 8/1965 | Fossler et al. | 383/13 |
| 3,262,283 | 7/1966 | Taylor | 383/13 |
| 3,456,865 | 7/1969 | Frank | 383/13 |
| 3,482,567 | 12/1969 | Franklin | 128/849 |
| 3,483,494 | 12/1969 | Cromie | 128/852 |
| 3,522,800 | 8/1970 | Lesser | 128/85 D |
| 3,546,643 | 12/1970 | Virostek | 335/303 |
| 3,654,047 | 4/1972 | Berkowitz | 428/129 |
| 3,727,658 | 4/1973 | Eldridge, Jr. | 128/852 |
| 3,861,521 | 1/1975 | Burtz | 206/63.3 |
| 4,013,109 | 3/1977 | Sandel | 206/818 |
| 4,051,845 | 10/1977 | Collins | 128/132 D |
| 4,100,684 | 7/1978 | Berger | 206/818 |
| 4,169,472 | 10/1979 | Morris | 128/854 |
| 4,336,806 | 6/1982 | Eldridge, Jr. | 335/303 |
| 4,485,919 | 12/1984 | Sandel | 206/523 |
| 4,524,767 | 6/1985 | Glassman | 128/854 |
| 4,733,806 | 3/1988 | Sloop | 206/523 |
| 4,944,311 | 7/1990 | Eldridge, Jr. | 128/849 |

Primary Examiner—Danton D. DeMille
Assistant Examiner—Michael Brown
Attorney, Agent, or Firm—Knobbe, Martens, Olson & Bear

[57] ABSTRACT

A reusable, flexible surgical drape which is laid over a patient adjacent the surgical field and which retains surgical instruments thereon to facilitate access to the instruments. A plurality of magnets are embedded in the drape so as to retain magnetizable instruments placed on the drape by means of magnetic force. A non-magnetized portion is provided in the center of the drape for storage of non-magnetizable instruments. A plurality of filaments extend upwardly from the nonmagnetic portion and aid in retaining the instruments in place. To prevent instruments from falling off the drape, the periphery of the drape is deformable to a non-planar orientation. A reusable pouch in which additional instruments are stored is removably secured to the drape. Ribs are provided on the interior of the pouch to maintain the walls of the pouch in a spaced relationship, and perforations are provided through the walls to permit sterilization of the pouch in an autoclave.

14 Claims, 2 Drawing Sheets

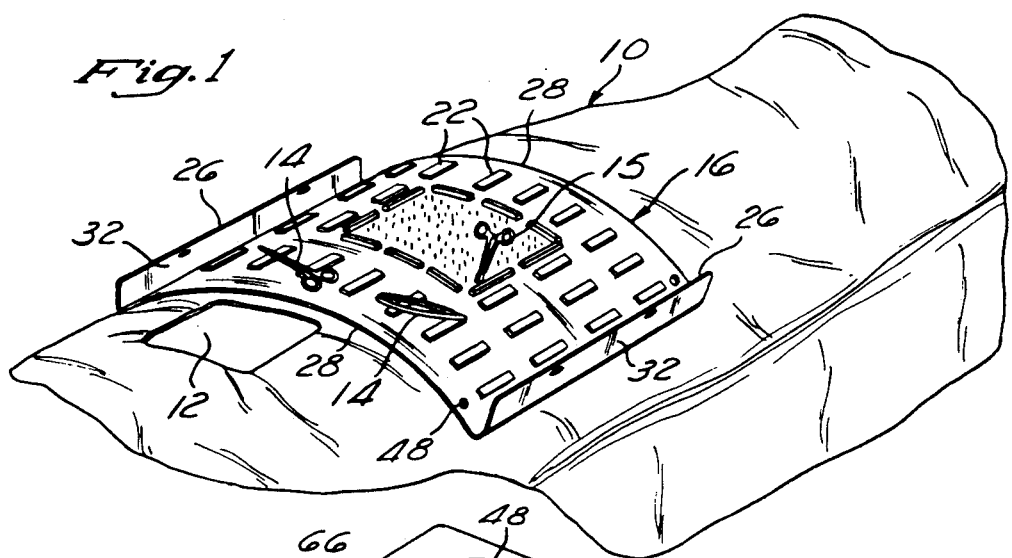
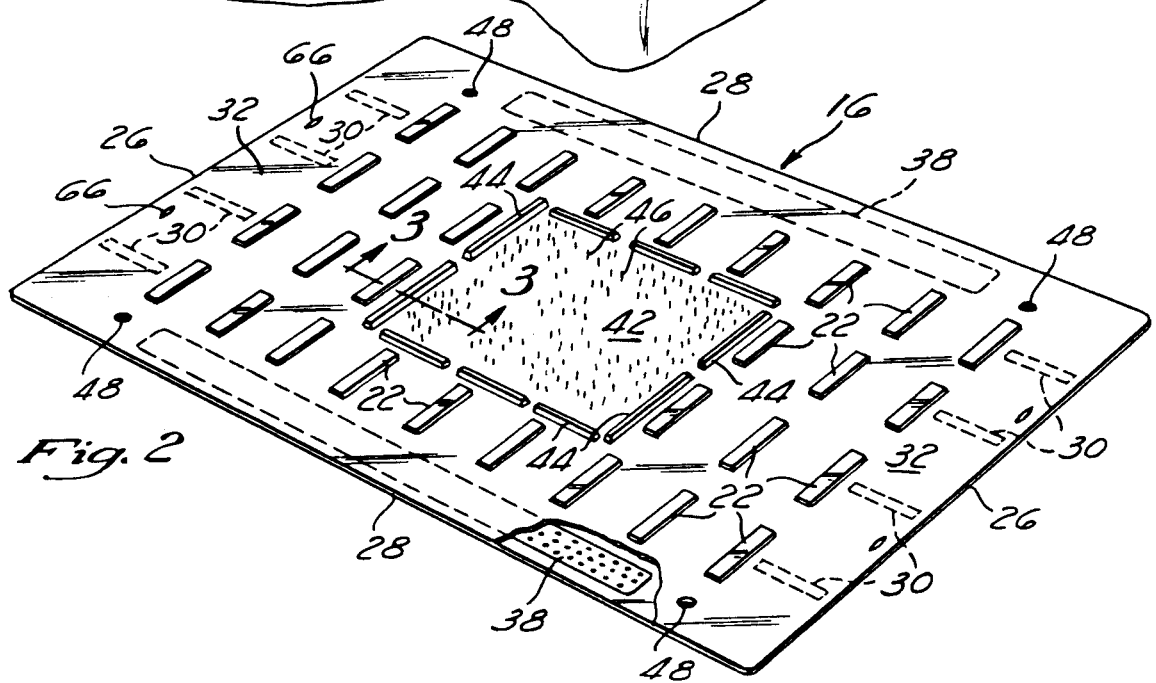
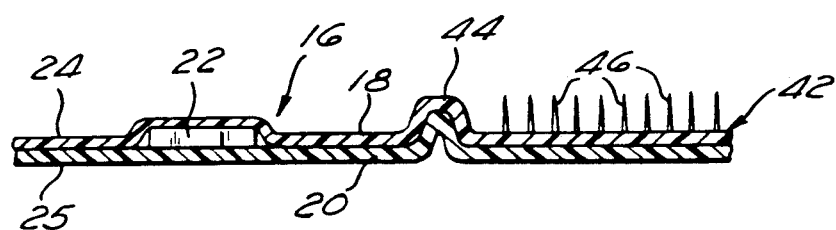
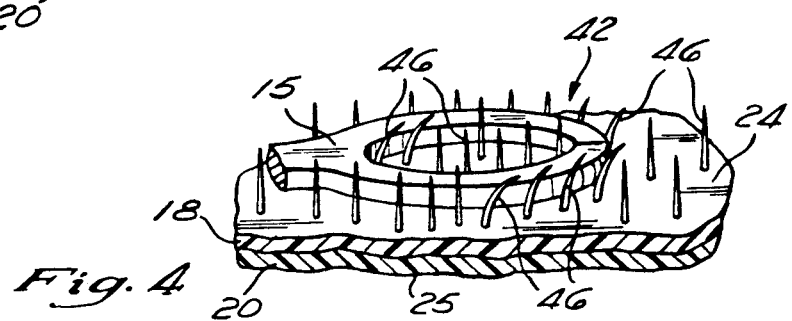

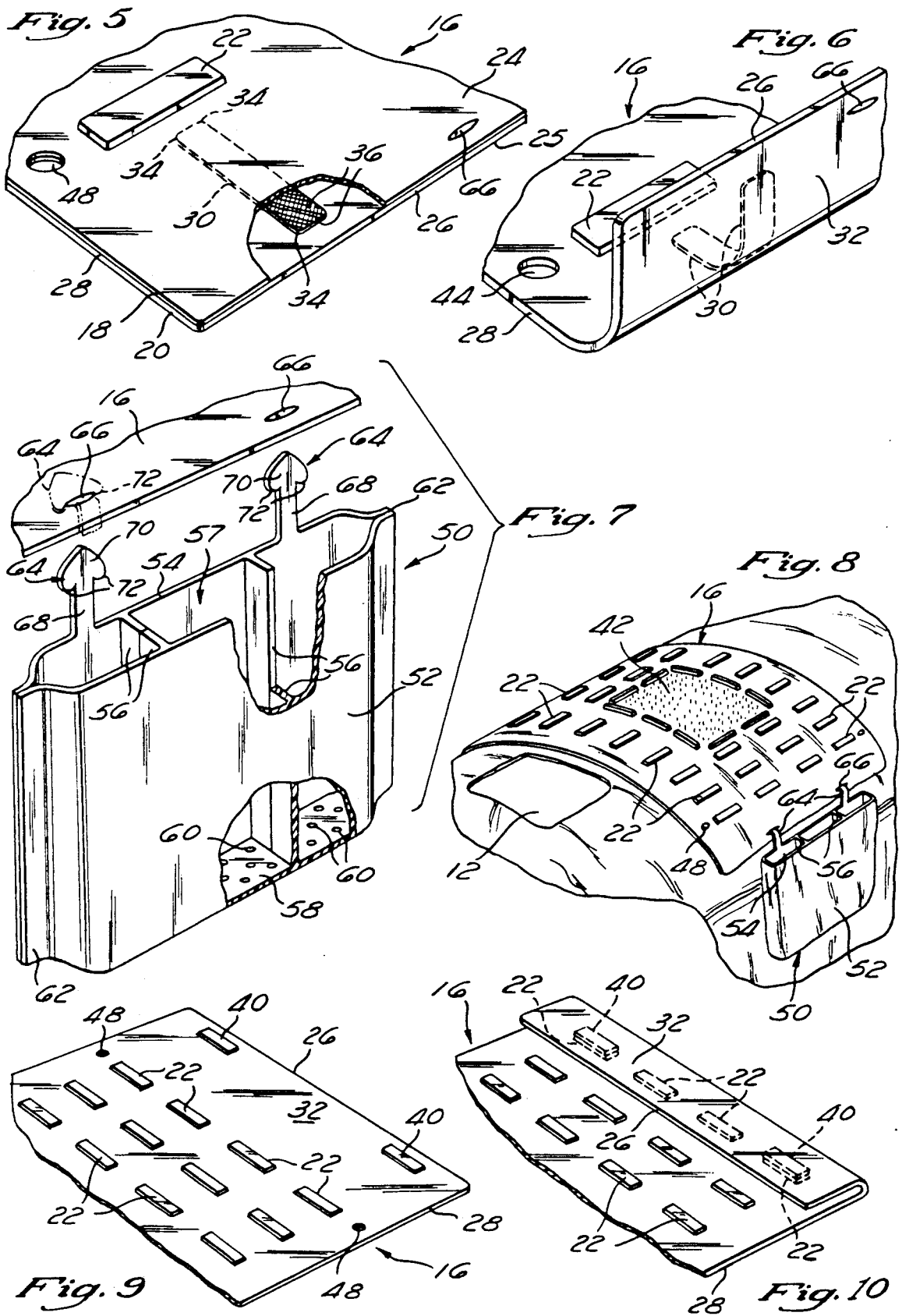

SERGICAL INSTRUMENT RETAINER

This application is a division of application Ser. No. 166,480, filed March 9, 1988. New U.S. Pat. No. 4,944,311.

BACKGROUND OF THE INVENTION

The present invention relates generally to the field of devices for retaining surgical instrument and more particularly to a surgical drape on which surgical instruments can be retained during surgery, and a pouch attached to the drape for the same purpose.

During surgery a wide variety of instruments are used by the surgeon, requiring the surgeon to frequently lay one instrument down on a sterile surface and then pick up another. To facilitate this handling of instruments, sterile magnetic surgical drapes have been developed which are laid on top of the patient, proximate the surgical field. The instruments can be laid on the drape by the surgeon and subsequently picked up without requiring time consuming reaching by the surgeon. Since these drapes conform to the patient, magnets are embedded in the drape to magnetically attract the instruments to the drape and prevent the instruments from sliding off the drape and onto the floor.

A major drawback of these prior magnetic surgical drapes is that instruments fabricated from a non-magnetizable material, such as plastic or brass, will not adhere to the drape. Further, certain magnetizable instruments are adversely affected by proximity to a magnetic field. For example, it is critical that needle clamps release a needle when desired. However, if the needle clamp or needle is exposed to a magnetic field and either becomes magnetized, then a magnetic attraction between the needle clamp and needle will prevent release of the needle at the desired time.

Another difficulty encountered with prior magnetic drapes has been that even magnetizable instruments have a tendency to fall off the drape if they are placed between the magnets. In addition to requiring resterilization, instruments that fall on the floor are an annoyance which can break the concentration of the surgeon. Also, falling instruments which enter the surgical field, or which are sharp, can be hazardous.

Another device which has been developed for retaining surgical instruments near the surgical field is a pouch which is secured to a surgical drape by means of towel clamps or tape. Previously, these pouches have not been reusable since they were unable to be effectively sterilized, thus limiting their usefulness. Another drawback of these pouches has been the difficulty associated with manipulating the towel clamps, which are separate from the pouch itself.

Thus, a need exists for a surgical drape on which non-magnetizable surgical instruments can be retained, and which prevents instruments from falling off the drape. Further, a need exists for a pouch which retains surgical instruments and which is reusable.

SUMMARY OF THE INVENTION

Briefly, the present invention is an apparatus for retaining surgical instruments adjacent a surgical field. The apparatus comprises a drape having a top surface on which surgical instruments are rested, and a bottom surface which lays on a patient. The drape is flexible so that the bottom surface of the drape conforms to the patient. A plurality of magnets are secured to the drape to retain surgical instruments which are placed on the top surface of the drape. The instrument-retaining magnets are oriented so that when a magnetizable surgical instrument is placed on the top surface of the drape, the force of magnetic attraction between the magnet and the instrument will cause the instrument to be retained in place.

A unique feature of the present invention is that a peripheral portion of the drape is maintained in a non-planar configuration. Advantageously, the peripheral portion prevents surgical instruments from falling off the drape in the event that insufficient magnetic attraction is achieved to retain the instrument on the top surface of the drape. Thus, the present drape minimizes the likelihood of instruments contacting non-sterile surfaces, or falling out of reach of the surgeon.

Preferably, the non-planar configuration of the peripheral portion of the drape is maintained by a means for reversibly causing deformation of the peripheral portion. For example, the deformation-causing means can comprise a deformable strip of metallic material secured to the drape by embedding the strip within the drape. Alternatively, deformation-causing means may comprise a peripheral magnet secured to the drape adjacent the non-planar peripheral portion. The peripheral magnet is spaced from the instrument-retaining magnets and oriented so that upon folding the drape along the space between the peripheral and instrument-retaining magnet, the magnets will be attracted when superimposed upon one another and will maintain the peripheral portion in a folded, non-planar position.

Since the peripheral portion can be reversibly deformed into a planar or non-planar configuration, the present surgical drape can be laid flat for easy shipping and handling, and also can be folded into a compact, planar shape.

Another feature of the present invention is the flexible surgical drape having a plurality of filaments extending upwardly from the top surface of the drape. The filaments engage a surgical instrument placed on the drape so as to prevent sliding of the instrument relative to the drape. Preferably, the filaments are sufficiently resilient in bending so as to deform under the weight of the surgical instrument which is placed directly on the filaments, and so that the adjacent filaments which are not caused to bend will surround and retain the surgical instruments on the top surface of the drape.

Advantageously, the filaments may be located on a non-magnetized portion of the drape which encompasses a sufficient area on the top surface of the drape so as to rest thereon a non-magnetizable surgical instruments or surgical instruments to which application of a magnetic field will have a deleterious effect. Preferably, a raised lip surrounds the non-magnetized portion of the drape so as to further aid in retaining instruments on the non-magnetized portion. As a result, the present surgical drape can be used in combination with surgical instruments which otherwise could not be retained in place on a drape which relied solely on magnets for retaining the instruments in place.

Another feature of the invention is a pouch in which surgical instruments may be stored. The pouch is comprised of a pair of substantially planar, spaced walls. The space between the walls defines an opening through which surgical instruments are inserted and withdrawn from the pouch. At least one rib extends along one of the walls that engages the other wall to maintain the walls in a spaced relationship. A major advantage of the present pouch as compared to the prior art is that access is permitted to the interior of the present pouch so that it can be sterilized and reused. To further aid in sterilization, the present pouch preferably includes a bottom wall which extends between the spaced walls, with the bottom wall including a plurality of perforations therein to allow passage of fluids therethrough.

Preferably, the present pouch can be removably secured to a surgical drape such as the instrument-retaining surgical drape of the present invention. The attachment means comprises a tab which mates with the slot in the surgical drape to removably secure the pouch to the drape. The tab itself comprises a neck extending from the pouch. The neck is sized to pass through the slot and terminates at one end in a head which is secured to the end of the neck. The head has a width greater than the slot so as to secure the neck to the slot. The head is bendable to reduce its width for passage of the head through the slot for attachment or removal of the pouch from the drape. The tabs can be reused after sterilization, unlike the prior art pouches which relied on tape to attach the pouch to a drape.

Advantageously, the entire pouch, including the tabs, can be formed from a single continuous sheet of flexible material which is folded over on itself and sealed at its sides to enclose the pouch. This construction technique is simple and economical, thus reducing the cost of producing the pouch. Further, since the tabs are integral with the pouch, no additional handling is required for the tabs, as opposed to the prior art towel clamps.

BRIEF DESCRIPTION OF THE DRAWINGS

FIG. 1 is a perspective view of the present surgical drape resting on a patient while in use during surgery.

FIG. 2 is a perspective view of the surgical drape shown in FIG. 1 with the drape in a fully planar orientation.

FIG. 3 is a cross-sectional view of the drape shown in FIG. 2, taken along line 3—3.

FIG. 4 is an enlarged partial perspective view of a surgical instrument resting on a non-magnetized portion of the present surgical drape.

FIG. 5 is an enlarged, partially cutaway perspective view of the corner of the present surgical drape and the deformable metal strip embedded in the drape.

FIG. 6 is a perspective view of the portion of the drape shown in FIG. 5, with the deformable metal strip bent so as to cause a non-planar orientation of the periphery of the drape.

FIG. 7 is a partially cutaway perspective view of the pouch of the present invention.

FIG. 8 is a perspective view showing the pouch of the present invention secured to the surgical drape of the present invention.

FIG. 9 is a partial perspective view of a second embodiment of the present surgical drape, in a planar position.

FIG. 10 is a perspective view of the second embodiment of the present surgical drape, having a peripheral portion in a non-planar orientation.

DETAILED DESCRIPTION OF THE PREFERRED EMBODIMENT

Referring to FIG. 1, a patient 10 is shown undergoing surgery. The patient 10 is covered by sterile sheets, with an opening provided in the sheets for access to the portion of the patient's body being operated on, referred to as the surgical field 12. A plurality of commonly used surgical instruments 14, 15 are shown resting on a surgical drape 16, constructed in accordance with one preferred embodiment of the present invention.

As is best seen in FIG. 3, the surgical drape 16 is formed from a top layer 18 of a thin flexible sheet which is secured or bonded to a bottom layer 20 of a thin flexible sheet. The layers 18 and 20 can be formed of rubber, or from a natural or synthetic thermoplastic.

A plurality of rectangular instrument retaining magnets 22 are secured to the drape 16 by embedding the magnets 22 within the drape, between the top and bottom layers 18, 20. The magnets 22 are spaced apart sufficiently to permit flexibility of the drape 16. The top layer 18 of the drape 16 defines an upwardly facing top surface 24 on which surgical instruments 14, 15 are rested, as shown in FIG. 1. The appropriate poles of the magnets 22 are oriented sufficiently close to the top surface 24 so that the force of magnetic attraction between the magnets 22 and instruments 14 which are magnetizable retains those instruments 14 on the top surface 24 of the drape 16. The bottom layer 20 of the drape 16 defines a bottom surface 25 which rests directly on the patient 10.

The drape 16 has a rectangular periphery which is defined by a pair of parallel short edges 26, and a parallel pair of long edges 28. As is best seen in Figures 2, 5 and 6, a plurality of thin, elongate deformable strips 30 are embedded within the drape 16 along peripheral portions 32 of the drape 16 adjacent the short edges 26. The deformable strips 30 extend between the outermost rows of magnets 22 and the short edges 26 of the drape 16, and are oriented substantially normal to the short edges 26. As illustrated in FIG. 5, the strips 30 are embedded between the top and bottom layers 18, 20 of the drape 16. To avoid tearing of the layers 18, 20, the strips 30 have rounded corners 34. Also, as shown in FIG. 5, to avoid tearing of the drape 16 the strips 30 are sandwiched between layers of Dacron 36.

When a manual bending force is applied to the strips 30, deformation of the strips 30 results, causing the peripheral portions 32 of the drape 16 in which the strips 30 are embedded to assume the contour of the strips 30. Thus, the peripheral portions 32 of the drape 16 can be maintained in a bent or non-planar configuration, as seen in FIGS. 1 and 6. The deformation of the strips 30 can be reversed so as to return the strips 30 and the peripheral portions 32 to a planar orientation, as in FIGS. 2 and 5. Preferably, the deformable stripe 30 are formed from a thin metallic material, however, other types of material may be substituted in place of metal.

FIG. 2 illustrates an alternate embodiment in which elongate deformable strips 38 embedded within the drape 16 extend alongside and parallel to the long edges 28 of the drape 16. These longer strips 38 are sufficiently wide so as to bend along their entire length, as opposed to the shorter strips 30 which are bent across their width. Preferably, the long strips 38 are perforated to facilitate bonding of the strips 38 to the drape 16. It is to be understood that the drape 16 may either include the longer strips 38 and shorter strips 30 alone or in any one of a number of possible combinations.

Another embodiment of the invention is shown in FIGS. 9 and 10. In order to maintain the peripheral portions 32 of the drape 16 in a bent or non-planar orientation, a pair of peripheral magnets 40 are secured to the drape 16 adjacent an edge, preferably a short edge 26. The peripheral magnets 40 are spaced sufficiently far from the outermost instrument retaining magnets 22 so as to enable the drape 16 to be folded over between the instrument retaining magnets and peripheral magnets such that the magnets 22, 40 are superimposed, as in FIG. 10. The poles of the magnets 22, 40 are oriented such that when superimposed, the magnets 22, 40 will be attracted, thus reversibly retaining the peripheral portion 32 of the drape 16 in a folded, non-planar configuration.

Referring now to FIGS. 1 through 4, a central portion of the drape 16 has no magnets therein, thus forming a non-magnetized portion 42 of the drape 16. The non-magnetized portion is bordered by a lip 44 which rises above the top surface 24 of the drape 16. The lip 44 is divided into a number of spaced, discreet segments so as to facilitate flexing and folding of the drape 16. A plurality of thin, hair-like filaments 46 extend upwardly from the non-magnetized portion 42. Preferably, each filament 46 is tapered so as to narrow toward the top of the filament 46, which aids in the molding of the filaments 46.

The non-magnetized portion 42 is sufficiently large in area so that a non-magnetizable surgical instrument 15 may be retained within the non-magnetized portion 42 of the drape 16. The filaments 46 are resilient and those directly under the instrument 15 will bend due to the weight of the instrument, as is best seen in FIG. 4. The unbent filaments 46 surrounding the instrument 15 will thus aid in preventing sliding movement of the instrument 15 relative to the drape 40. Although not shown, the filaments 46 may alternatively cover the entire top surface 24 of the drape 16, including magnetized portions.

Holes 48 are provided through the drape 16 adjacent the corners of the drape 16 to enable towel clamps (not shown) to be removably secured to the drape 16.

In operation, the drape 16 is laid on the patient 10 adjacent the surgical field 12. The flexibility of the drape 16 permits the bottom surface 25 to conform to the patient 25, so that the drape 16 assumes a roughly cylindrical curvature about an axis parallel to its short edges 26. The peripheral portions 32 of the drape 16 adjacent the short edges 26 are then deformed into a non-planar position, such that the peripheral portions 32 extend substantially normal to the remainder of the drape 16.

During the course of surgery, magnetizable instruments 14 are placed on the top surface 24 of the drape 16 for temporary storage. The instrument retaining magnets 22 will cause the instruments 14 to be attracted to the drape 16, preventing the instruments 14 from sliding off the drape 16. Non-magnetizable instruments 15, and instruments on which a magnetic field will have a deleterious effect, are placed on the non-magnetizable portion 42 of the drape 16, where the filaments 46 and lip 44 aid in retaining the instrument 15 in place.

In the event an instrument 14, 15 is placed on the drape 16 in such a manner that it is not properly retained by the drape 16, the deformed peripheral portions 32 of the drape 16 will stop the instrument 14, 15 from falling off the drape 16 completely. By aligning the deformed peripheral portions 32 parallel to the axis of curvature of the drape 16, the peripheral portions 32 are adjacent the ends of the drape 16 which assume the greatest slope from a horizontal plane, and thus are the most likely portions of the drape 16 from which instruments will fall.

Turning now to FIG. 7 and 8, a pouch 50 is shown which is designed to be removably attached to the drape 16. The pouch 50 includes a substantially planar front wall 52 and a substantially planar back wall 54. The front and back walls 52, 54 are substantially parallel and spaced from each other by means of ribs 56 which extend from the interior surfaces of the walls 52, 54. Although not shown, the ribs 56 alternatively may be staggered relative to each other. The spacing between the walls 52, 54 defines an opening 56 at the top of the pouch 50 through which surgical instruments (not shown) may be passed.

The front and back walls 52, 54 are joined along their lower ends by a bottom wall 58 which has a plurality of perforations 60 therein. Seams 62 are also provided to join the side edges of the front and back walls 52, 54.

To removably secure the pouch 50 to the drape 16, a pair of tabs 64 are formed integral with the pouch 50. The tabs 64 are configured to extend through slots 66 in the drape 16 to secure the pouch 50 to the drape 16. The tabs 64 are formed by elongate necks 68 which extend upwardly from the back wall 54 of the pouch 50. The width of the neck 68 is equal to or less than the length of the slot 66, so that the necks 68 can slide freely through the slots 66. The necks 68 each terminate at a head 70 which is wider than the neck 68, and wider than the slot 66. The heads 70 are formed from a flexible material so that they can be folded to reduce their width, enabling the head 70 to slip through the slot 66, as shown in broken lines in FIG. 7.

To prevent unwanted slippage of the head 70 back out of the slot 66, the head 70 includes a pair of rounded lobes 72 which depend downwardly from the head 70 on either side of the neck 68. The lobes 72 extend beyond the point of attachment between the head 70 and the neck 68 so that the lobes 72 overlap the slot 66 and prevent the head 70 from being drawn through the slot 60, so as to support the weight of the pouch 50 and any instruments retained therein.

The entire pouch 50 may be formed from a single sheet of flexible material which is folded about the bottom wall 58 and heat sealed together along the side seams 62. The perforations 60 and the tabs 64 can be die cut from the sheet.

In operation, the pouch 50 is secured to the drape 16 by passing the heads 70 of the tabs 64 through the slots 66 and drawing the heads 70 back so that the lobes 72 overlap the slots 66. During surgery, various instruments are placed in the pouch 50 for storage, such as cautery devices and suction devices which are too large to be placed on the drape 16 or which have hoses or wires extending therefrom which would become entangled with the other instruments 14, 15 on the drape 16. While in the pouch 50, liquids on the instruments can drain through the perforations 60.

After surgery, the pouch 50 is removed from the drape 16 by folding the tab heads 70 and drawing them through the slots 66. The pouch 50 can then be sterilized by any of a number of means, such as in a gas or steam autoclave (not shown). Since the ribs 56 maintain the front and back walls 52, 54 of the pouch 50 spaced apart, fluids can enter the pouch 50 through the opening 56 when in the autoclave. The perforations 60 in the bottom wall 58 also encourage the passage of fluids through the pouch 50, further aiding sterilization. Since the tabs 64 are integral with the pouch 50, no additional handling is required during sterilization, nor can the tabs 64 be misplaced. The pouch 50 is reusable after sterilization.

It is to be understood that the pouch 50 may be secured to any of a variety of structures having slots therein, although in the preferred embodiment the pouch 50 is attached to the magnetic drape 16 of the present invention.

Although the present invention has been described with reference to the preferred embodiments, numerous modifications and rearrangements can be made which will still come within the scope of the invention.

What is claimed is:

1. An apparatus for retaining surgical instruments adjacent a surgical field, comprising:

drape having a top surface on which surgical instruments are rested and a bottom surface which lays entirely on a patient, said drape being flexible so as to conform to said patient;

plurality of instrument-retaining magnets secured to said drape and oriented so that when a magnetizable surgical instrument is placed on said top surface of said drape adjacent one of said magnets, the force of magnetic attraction between said magnet and said instrument will cause said instrument to be retained in place on said top surface of said drape;

a peripheral portion of said drape being maintained in a non-planar configuration by extending upwardly, away from said patient, said peripheral portion preventing surgical instruments from falling off said drape during a surgical procedure in the event that insufficient magnetic attraction is achieved to retain said instrument on said top surface, said drape thereby retaining and providing access to said surgical instruments so as t enable repeated placement of said instruments on said drape and removal of said instruments from said drape during the course of a surgical procedure; and means for reversibly causing deformation of said peripheral portion of said drape, said deformation causing means maintaining said non-planar configuration of said peripheral portion.

2. The apparatus of claim 1, wherein said deformation causing means comprises a deformable strip of metallic material secured to said drape.

3. The apparatus of claim 2, wherein said deformable strip has a plurality of apertures and is embedded within said drape.

4. The apparatus of claim 2, wherein:

said peripheral portion is defined by an edge of said drape; and said strip being elongate and extending substantially normal to said edge.

5. The apparatus of claim 4, wherein said strip extends between said magnets and said edge.

6. The apparatus of claim 2, wherein said strip has rounded corners.

7. The apparatus of claim 1, wherein said deformation causing means comprises a peripheral magnet secured to said drape adjacent said peripheral portion, said peripheral magnet being spaced from said instrument retaining magnets and oriented so that, upon folding said drape along said space between said peripheral and instrument retaining magnets, said magnets will be magnetically attracted when superimposed on one another and will maintain said peripheral portion in a folded, non-planar position.

8. The apparatus of claim 1, wherein said drape further comprises an integral, non-magnetized portion which encompasses a sufficient area on said top surface of said drape so as to rest thereon non-magnetizable surgical instruments or surgical instruments to which application of a magnetic field will have a deleterious effect.

9. The apparatus of claim 8, wherein said non-magnetized portion is flexible and is surrounded by a flexible lip which is raised above said top surface, so as to aid in retaining said instruments on said non-magnetized portion.

10. The apparatus of claim 9, wherein said non-magnetized portion is substantially centered within said drape and is surrounded by said magnets.

11. The apparatus of claim 1, wherein said peripheral portion is integral with said drape.

12. An apparatus for retaining surgical instruments adjacent a surgical field, comprising:

a drape having a top surface on which surgical instruments are rested and a bottom surface which lays entirely on a patient, said drape being flexible so as to conform to said patient;

a plurality of instrument-retaining magnets secured to said drape and oriented so that, when a magnetizable surgical instrument is placed on said top surface of said drape adjacent one of said magnets, the force of magnetic attraction between said magnet and said instrument will cause said instrument to be retained in place on said top surface of said drape; and a non-magnetized portion of said drape which encompasses a sufficient area on said top surface of said drape so as to rest thereon non-magnetizable surgical instruments or surgical instruments to which application of a magnetic field will have a deleterious effect wherein said non-magnetized portion is positioned substantially within the center of said drape.

13. The apparatus of claim 12, wherein said non-magnetized portion is integral with said drape.

14. An apparatus for retaining surgical instruments adjacent a surgical field, comprising:

a drape having a top surface on which surgical instruments are rested and a bottom surface which lays entirely on a patient, said drape being flexible so as to conform to said patient;

a plurality of instrument-retaining magnets secured to said drape and oriented so that, when a magnetizable surgical instrument is placed on said top surface of said drape adjacent one of said magnets, the force of magnetic attraction between said magnet and said instrument will cause said instrument to be retained in place on said top surface of said drape; and a non-magnetized portion of said drape which encompasses a sufficient area on said top surface of said drape so as to rest thereon non-magnetizable surgical instruments or surgical instruments to which application of a magnetic field will have a deleterious effect, wherein said non-magnetized portion is flexible and is surrounded by a flexible lip which is raised above said top surface, so as to aid in retaining said instruments on said non-magnetized portion.

* * * * *